United States Patent
Frodl et al.

(10) Patent No.: US 7,326,931 B2
(45) Date of Patent: Feb. 5, 2008

(54) GAS SENSOR ASSEMBLY AND MEASUREMENT METHOD WITH EARLY WARNING MEANS

(75) Inventors: Robert Frodl, München (DE); Thomas Tille, München (DE)

(73) Assignee: Tyco Electronics Raychem GmbH, Ottobrunn (DE)

( * ) Notice: Subject to any disclaimer, the term of this patent is extended or adjusted under 35 U.S.C. 154(b) by 0 days.

(21) Appl. No.: 11/457,294

(22) Filed: Jul. 13, 2006

(65) Prior Publication Data

US 2007/0017458 A1 Jan. 25, 2007

(30) Foreign Application Priority Data

Jul. 13, 2005 (DE) .................. 10 2005 032 722

(51) Int. Cl.
  *G01J 5/02* (2006.01)
(52) U.S. Cl. .................................. 250/343
(58) Field of Classification Search ......... 250/343
  See application file for complete search history.

(56) References Cited

U.S. PATENT DOCUMENTS

| | | | |
|---|---|---|---|
| 4,437,005 A | | 3/1984 | Ophoff et al. |
| 4,709,150 A | * | 11/1987 | Burough et al. ......... 250/338.1 |
| 5,347,474 A | | 9/1994 | Wong |
| 5,900,533 A | * | 5/1999 | Chou ....................... 73/24.01 |
| 6,825,471 B1 | | 11/2004 | Shulga et al. |
| 6,843,102 B1 | | 1/2005 | Shulga et al. |
| 7,075,653 B1 | * | 7/2006 | Rutherford .................. 356/437 |
| 7,166,842 B2 | | 1/2007 | Minuth et al. |

FOREIGN PATENT DOCUMENTS

| | | |
|---|---|---|
| DE | 10221708 A1 | 12/2003 |
| DE | 1020040928077 A1 | 12/2005 |
| EP | 0651244 A1 | 5/1995 |
| WO | 0054032 A | 9/2000 |

* cited by examiner

*Primary Examiner*—David Porta
*Assistant Examiner*—Mark R Gaworecki
(74) *Attorney, Agent, or Firm*—Barley Snyder LLC

(57) ABSTRACT

The invention relates to a method for measuring the presence and/or the concentration of an analyte using a gas sensor assembly and to a corresponding gas sensor assembly. The gas sensor assembly comprises, in particular, a radiation-emitting radiation source (102), a gas measurement chamber (104) which may be filled with a test gas (110) containing the at least one analyte to be measured, and at least one detector device (108) which detects the radiation (116) and generates an output signal which is dependent on the presence and/or the concentration of the analyte. In order to meet increased safety requirements and to avoid the drawbacks of the known systems without inadmissible increased complexity and overall size, the radiation source emits radiation in the form of pulses and, during each radiation pulse, a large number of individual values (304) are recorded for generating an average measured value, the first of the large number of individual values being compared, during the first radiation pulse, with a predetermined threshold value and an alarm signal (136) being generated if the threshold value is exceeded.

14 Claims, 4 Drawing Sheets

GAS SENSOR ASSEMBLY AND MEASUREMENT METHOD WITH EARLY WARNING MEANS

FIELD OF THE INVENTION

The present invention relates to a method for measuring the presence and/or the concentration of an analyte using a gas sensor assembly and to a corresponding gas sensor assembly.

BACKGROUND

Gas sensor assemblies of this type are known for the detection of a broad range of analytes, for example carbon dioxide or methane. Conventional gas sensors, as disclosed, for example, in DE 10 2004 028 077.0, are based on the property of many polar gases to absorb radiation in the infrared wavelength range. Gases of this type consist of two different kinds of atoms such as $CO_2$, but also CO and $NO_x$, and all hydrocarbons such as methane, propane or other natural gases used for heating.

The IR light is able, by cooperating with the dipole moment of the polar molecule, to stimulate the molecules by stimulating rotational and vibratory oscillations. The heat energy of the IR light is thus transmitted to the gas and, in the same way, the intensity of an IR beam passing through a gas volume is reduced. Absorption takes place, in accordance with the stimulated states, at a respective wavelength characteristic of the gas in question—in the case of $CO_2$, for example, at 4.24 μm.

It is therefore possible, using an infrared gas sensor of this type, to establish the presence of a gas component and/or the concentration of this gas component in a test gas. Gas sensors of this type comprise a radiation source, an absorption path, i.e. a measurement chamber in which the gas to be detected is contained, and a radiation detector. The radiation intensity measured by the radiation detector is, according to Lambert-Beer's Law, an indicator of the concentration of the absorbing gas as expressed by the following equation:

$$I=I_0 \exp(-kcl)$$

wherein I denotes the measured intensity, $I_0$ the irradiated intensity, k a constant, c the concentration of the corresponding gas in molecules per unit of volume, and l the length of the measurement path.

In the case of what are known as NDIR (non dispersive infrared) sensors, a broadband IR source is conventionally used as the radiation source and the relevant wavelength is adjusted via an interference filter or screen. Alternatively, a selective radiation source, for example a light-emitting diode or a laser, may also be used in combination with non-wavelength-sensitive radiation receivers.

Carbon dioxide detection, in particular, is becoming increasingly important in a large number of fields of application. For example, the quality of internal air may be monitored both in relation to the operation of motor vehicles. Also, the cleaning cycles of self-cleaning ovens and the feeding of plants with $CO_2$ in greenhouses may be regulated. In the medical field, for example in anaesthetics, the air inhaled by a patient may be monitored and, finally, a carbon dioxide sensor may be used in an associated warning system wherever there is a risk of $CO_2$ escaping, for example in the context of correspondingly filled air-conditioning systems.

In automotive engineering, carbon dioxide detection may be used, in order to increase energy efficiency during heating and air conditioning, to monitor the $CO_2$ content of the internal air in order, if required, i.e. in the event of a high $CO_2$ concentration, to cause a supply of fresh air via a corresponding fan shutter activation means. In addition, modern vehicle air-conditioning systems are based on $CO_2$ as the coolant, so in automotive engineering $CO_2$ gas sensors may also perform a monitoring function in relation to $CO_2$ escaping in the event of any defects. In automotive engineering, in particular, gas sensors of this type have to meet extremely stringent robustness, reliability and miniaturization requirements.

The radiation source of known gas sensor assemblies is often not operated continuously, but rather pulsed at a specific frequency. A constant frequency and a specific pulse-duty ratio is usually selected, the pulse-duty ratio designating the ratio of the on-time (pulse width) to the period time. Disturbances may be reduced by using, during signal processing in the detector region, a narrow-band filter, the filter frequency of which corresponds to the pulse frequency at which the radiation source is pulsed.

As described in DE 10 2004 028 077.0, gas sensor assemblies in which the radiation source is pulsed have the problem, both during start-up of the system and in operating modes in which the radiation sources do not emit any light for a relatively long period of time, that the settling time, i.e. the time before usable test results are available, is comparatively long. In an infrared-based gas sensor operated in a pulsed manner, for example, the system therefore has to settle thermally for such a long time that the first 10 to 15 measured values are unusable. In current designs, it takes from approximately 5 to 10 seconds after start-up until a first reliable measured value is available. However, this is problematic in relation to safety applications, in particular in cases in which the system has to be switched on and off relatively frequently.

SUMMARY

An object of the present invention is therefore to provide a method for measurement using a gas sensor assembly and also a generic gas sensor assembly which meets increased safety requirements and is able to prevent the drawbacks of the known systems without inadmissible increased complexity and overall size.

The present invention is based on the fact that, in pulse mode, the radiation source remains switched on for a specific on-time and, during this time, the signal at the detector is boosted. During the pulse time, integration takes place via a large number of individual measurements, generally several hundred to one thousand. This integration leads to an average measured value and is carried out to allow the noise effects to be eliminated. After the pulse, the radiation source is switched off for a specific period of time until the following measurement cycle begins. It may be demonstrated that a specific number of measurement pulses of this type are necessary before the overall system is in thermal equilibrium and the average measured value obtained from the individual values is a reliable measured value. In current designs, this time is from approximately 5 to 10 seconds.

In order to ensure increased safety, the first individual measurement is used as early as the first pulse after start-up of the sensor system in order to estimate an anticipated value of the average measurement signal. If the estimated value exceeds a specific threshold, an alarm signal is immediately issued as an early warning. The use of $CO_2$ gas sensors as safety sensors therefore allows a warning to be issued immediately after start-up if there is a dangerous concentration of gas. Examples of this would include opening a car door using the locking system. According to the invention, it may be determined prior to or during opening whether there is a dangerous concentration in the passenger compartment. In the case of $CO_2$, the values for a normal atmosphere (from approximately 350 to 1,500 ppm) are sufficiently remote from the conventional alarm thresholds (from 10,000 to 20,000 ppm) to allow false alarms to be substantially ruled out in the method according to the invention.

According to an advantageous embodiment of the present invention, an estimated value for the average measured value is formed from the first individual value and the threshold value is a maximum permissible average measured value. This allows both optimally reliable detection of dangerous gas concentrations to be achieved immediately after start-up of the sensor system and the likelihood of false alarms to be effectively reduced.

According to an advantageous embodiment, in the step of the comparison with the threshold value, an estimated value for the average measured value is formed during the first pulse and compared with a maximum permissible average measured value as the threshold value. As the courses of the curves generally proceed in a highly defined manner during a radiation pulse, the overall course of the detector signal may be predicted during the first pulse from the first individual value, with reference to stored reference courses, and a statement may be issued as to whether there is likely to be an increased concentration of gas. An alarm signal may thus be issued and increased safety achieved particularly rapidly.

It is known that after start-up the overall gas sensor system must thermally settle and the average sensor signals measured after the first pulses have a characteristic time curve which is, however, also subject to specific physical laws and may therefore be predicted.

The average measured values of those radiation pulses at which the gas sensor system is in the settled state may therefore be concluded from the average measured value for the first pulse. In order, therefore, to be able to predict as accurately as possible the actual concentration of gas, an estimated value for the expected end value in the settled state may, according to an advantageous embodiment of the present invention, be obtained from the first individual measurement and compared to a corresponding threshold value.

The two possibilities for estimation, i.e. derivation of an expected average measured value for the first pulse and comparison with a threshold value defined for the first pulse, or else the calculation of an estimated value for the expected end value in the thermally settled state, may be applied as alternatives or in combination. For example, an estimated value for the average measured value expected during the first measured pulse may firstly be calculated during a radiation pulse, with the aid of the stored curve, from the first individual measured value, and this estimated value for the average measured value may then be used, by comparison with a stored settling behaviour of the gas sensor system, in order to calculate an expected end value. This estimated value may then be compared with a threshold value for the end value and the alarm signal may be issued when the threshold value is exceeded. This allows the alarm to be triggered particularly rapidly in hazardous situations and false alarms are prevented as far as possible.

The settled state, i.e. the curve of the average measured values for a number of pulses as a function of time, is achieved, for example, in accordance with a PID controller characteristic and the corresponding description of a characteristic of this type may, according to the invention, be stored in the control means of the gas sensor assembly and used for calculating the estimated end value.

In order also to be able to correct the measured values with respect to temperature and to have an indication of the occurrence of the thermal equilibrium, the gas sensor assembly may also be equipped with a temperature probe which monitors the temperature of the wall of the gas measurement chamber or the temperature in proximity to the radiation source.

The advantageous characteristics of the gas sensor assembly according to the invention may, in particular, be used for the detection of carbon dioxide, for example in automotive engineering, both for monitoring $CO_2$ escaping at leakage sites and for inspecting the quality of air in the passenger compartment. However, the gas sensor assembly may, of course, also be used for the detection of any other polar gases.

BRIEF DESCRIPTION OF THE DRAWINGS

The invention will be described hereinafter in greater detail with reference to the advantageous configurations illustrated in the drawings. Similar or corresponding details of the subject-matter according to the invention are provided with identical reference numerals. In the drawings.

DETAILED DESCRIPTION OF THE EMBODIMENTS OF THE INVENTION

The construction and the mode of operation of the gas sensor assembly according to the invention will be described hereinafter in greater detail with reference to the figures.

Figure 1:
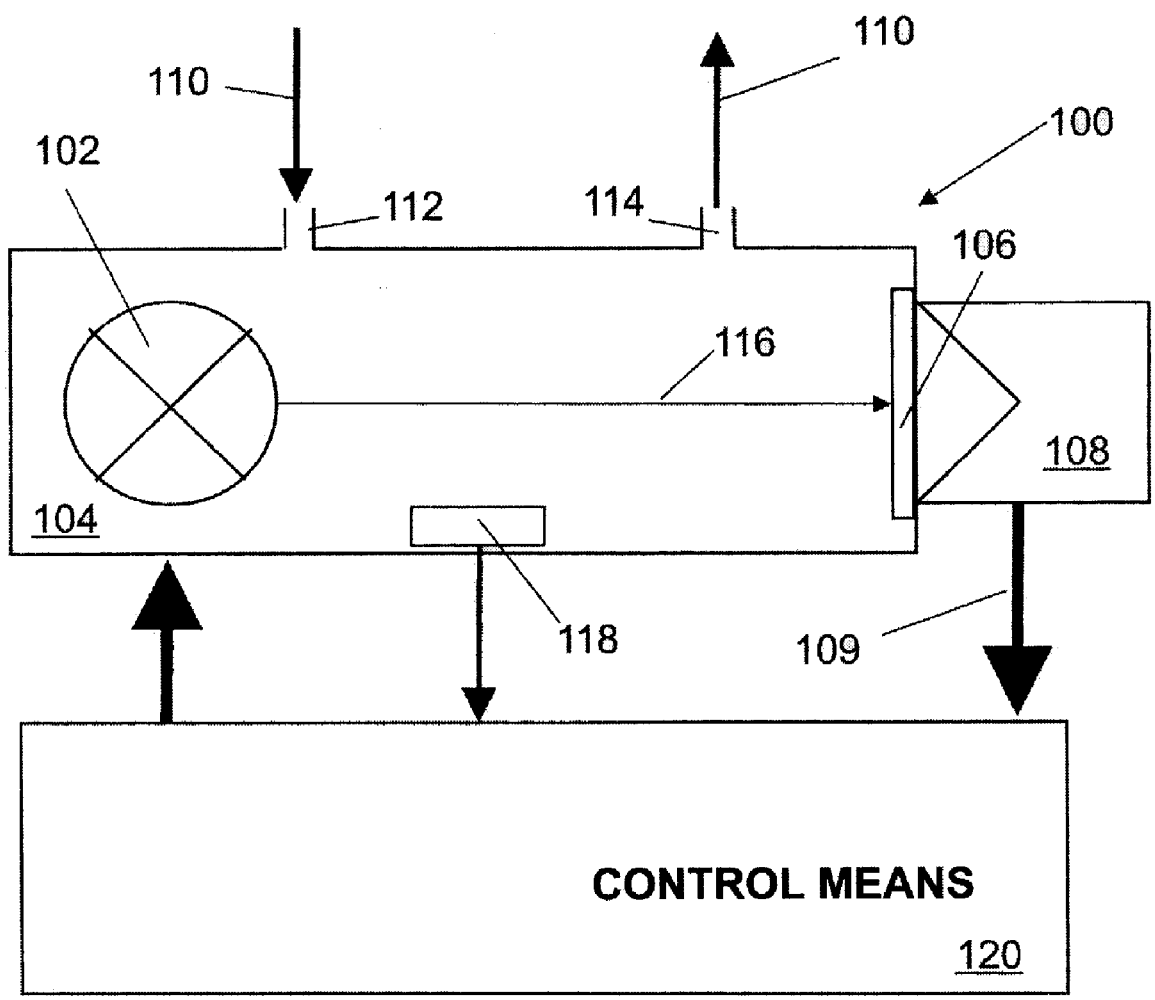
FIG. 1 is a schematic view of a gas sensor assembly according to an advantageous embodiment.

As shown in FIG. 1, the gas sensor assembly 100 according to the invention comprises a radiation source 102, in this case a broadband infrared radiation source. The illustrated gas sensor assembly 100 is, in principle, what is known as an NDIR (non dispersive infrared) sensor. The basic components, apart from the infrared radiation source 102, are the gas measurement chamber 104, a wavelength filter 106 and an infrared detector 108.

The test gas 110, which is to be examined for the gas component to be detected, is pumped into the gas measurement chamber 104 or diffused therein, through inlets and outlets 112, 114. The presence and/or the concentration of the desired gas may be determined, as described above, electro-optically via the absorption of a specific wavelength in the infrared range. The emitted infrared radiation 116 is guided through the gas measurement chamber 104 to the detector 108. The detector 108 comprises an optical filter 106 which passes only that wavelength range in which the gas molecules to be detected absorb. Other gas molecules do not normally absorb light at this specific wavelength and therefore also do not influence the amount of radiation which reaches the detector 108.

The detector 108 may be in the form of any suitable infrared detector and the method according to the invention may be adapted to the respective type of detector.

The detector 108 may, for example, be a pyro-element, an infrared thermopile or a photodiode. Each suitable detector should be selected in accordance with the respective requirements. Photodiodes have the advantage of being comparatively inexpensive components, whereas thermal columns, as thermopile detectors, have the advantage of particularly high and uniform absorption of the radiation in the selected spectral range. Finally, pyroelectric sensors have the advantage of being highly sensitive and producible in miniaturized form.

The IR signal from the radiation source 102 is pulsed to allow thermal background signals to be filtered out from the desired signal. A control means 120 both activates the radiation source 102 and receives and processes the output signals from the detector 108. In particular, it supplies a regular output signal and an alarm signal for an early warning.

A temperature probe 118 may also be provided for detecting the temperature in the gas measurement chamber 104.

Figure 2:
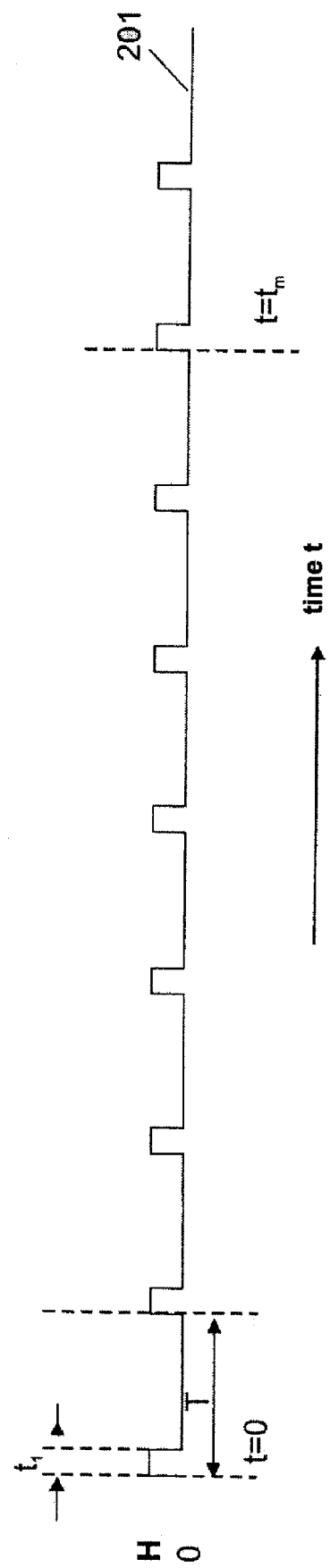
FIG. 2 is a diagram of the radiation pulses emitted from the radiation source in FIG. 1 as a function of time.

FIG. 2 shows schematically the time characteristic for the light signal emitted from the radiation source 102 in FIG. 1. The base line denotes the switched-off state and the high-level line the switched-on state of the radiation source. The curve 201 indicates the time conditions for operation at a constant pulse sequence.

At the moment t=0, the system is started up and the radiation source 102 starts to emit light pulses according to the curve 201. However, after start-up, the gas sensor system must first thermally settle and a number of measured values (for example 10 to 15) are therefore unusable, so actual measurement cannot start until the time $t=t_m$. However, in order to allow an early warning as early as the start of the pulse sequence shown in FIG. 2, at least in the event of dangerously high concentrations of gas, the very first measured value is, according to the invention, evaluated as early as the second radiation pulse in order to be able to estimate whether there is a dangerous concentration of gas.

Figure 3:
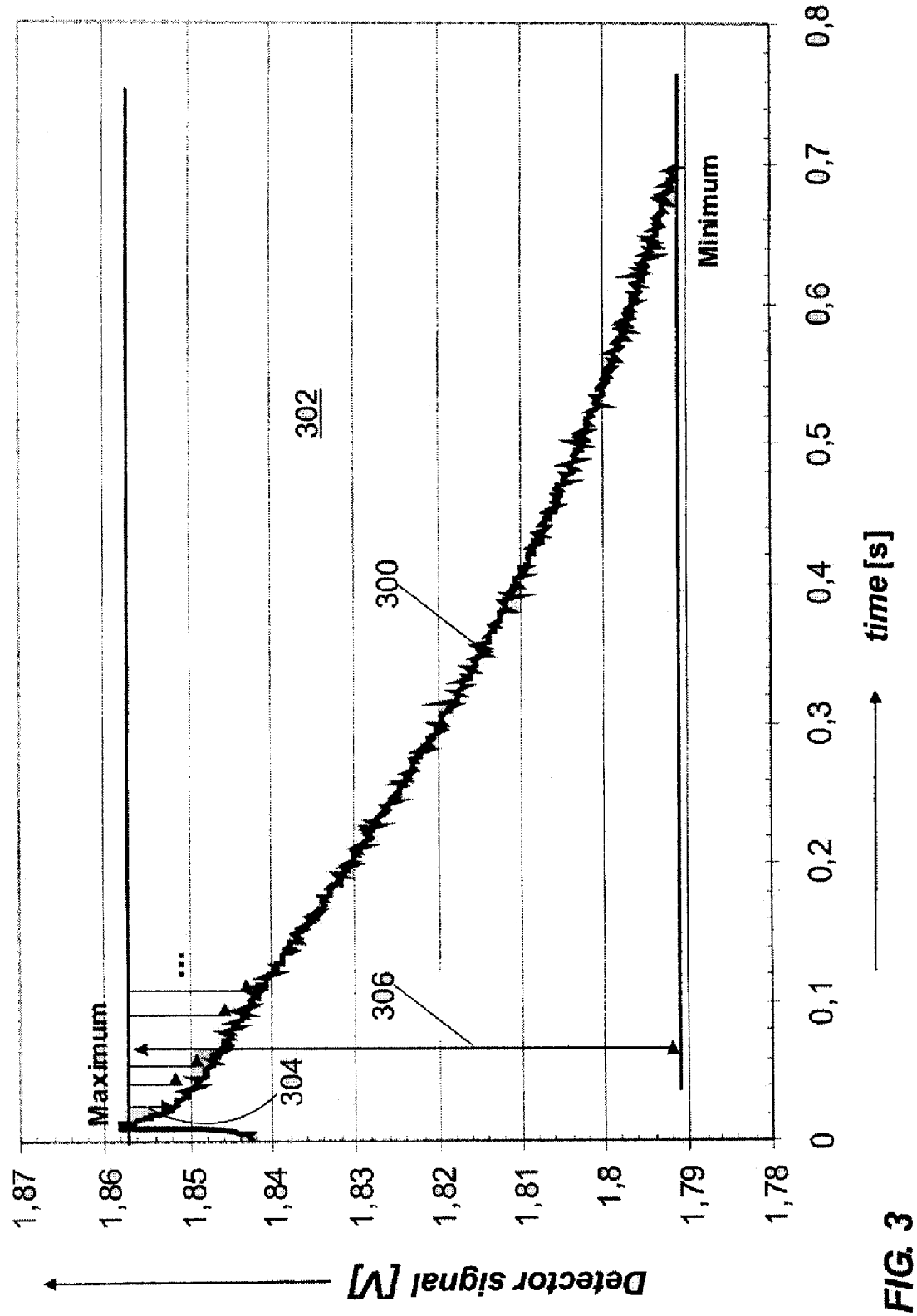
FIG. 3 shows the course of the detector signal as a function of time during the first current pulse from FIG. 2.

FIG. 3 will be examined to allow a more detailed description. In this figure, the detector signal 109, supplied by the detector 108, is plotted as the measurement curve 300 as a function of time during the first voltage pulse in FIG. 2.

In order to allow as much noise as possible to be eliminated, several hundred to one thousand individual measurements are carried out and the individual values 304 are integrated during this period of, for example, 0.8 seconds.

The integral 302, symbolized by the plane in FIG. 3, is used as the average measured value for the first pulse. According to the invention, the first individual value 304 is used as early as the first pulse after the gas sensor unit has been switched on, in order to predict a likely end value using an estimation. If the estimated value exceeds a predetermined threshold, an alarm signal may be issued.

According to an embodiment of the invention, this estimation is carried out in two stages. Firstly, the course of the curve 300 may be predicted and an estimated value for the integral 302 determined from the individual value 304 using stored curves.

In a subsequent stage, an estimation for the integral value in the settled state, i.e. for times $t>t_m$, may be determined from the estimated integral value, which represents an estimated mean value, and knowledge of the thermal behavior of the gas sensor assembly during settling. The settling characteristic may, for example, resemble a PID controller characteristic, and an estimation of the expected end value may therefore be determined right from the first individual measurement. If the estimated end value exceeds a predefined threshold value, it must be assumed that the gas concentration levels are excessively high and an alarm may be triggered immediately. If the estimated value is below the critical threshold value, the measurement is regularly continued, i.e. the integrals for the first pulse and all subsequent pulses are formed until the settled state has been reached and, after a time $t>t_m$, a regular measurement signal is issued.

According to an advantageous development of the present invention, if the first individual value 304 has not led to the triggering of an alarm, the subsequent measure values are used in order further to improve the respective estimation during the integration phase. The estimated value thus corresponds, at the end of the integration phase of the first pulse, to the actual average measured value for the first pulse. The estimated value for the end value may therefore also be constantly improved over the course of the subsequent pulses.

In the event of a detection of $CO_2$, the values for a normal atmosphere, at from approximately 350 to 1500 ppm, are sufficiently remote from the conventional alarm thresholds, which are set at from 10,000 to 20,000 ppm, to all but rule out the possibility of a false alarm. Since the hazardous limit value is therefore sufficiently remote from the ambient conditions, a comparatively reliable early warning of a hazardous concentration may be issued despite the significant estimation errors. This occurs as soon as the predefined warning threshold has been exceeded. In such cases, the actual measured value follows the alarm message. The early warning device according to the invention thus allows the time preceding the hazardous gas concentration warning to be substantially shortened immediately after start-up of the gas sensor system.

It will be noted from FIG. 3 that, in the actual time characteristic, the schematically illustrated individual values are, of course, much more tightly packed in the pulse integration phase, and the present illustration was selected purely for the purposes of basic explanation.

Figure 4:
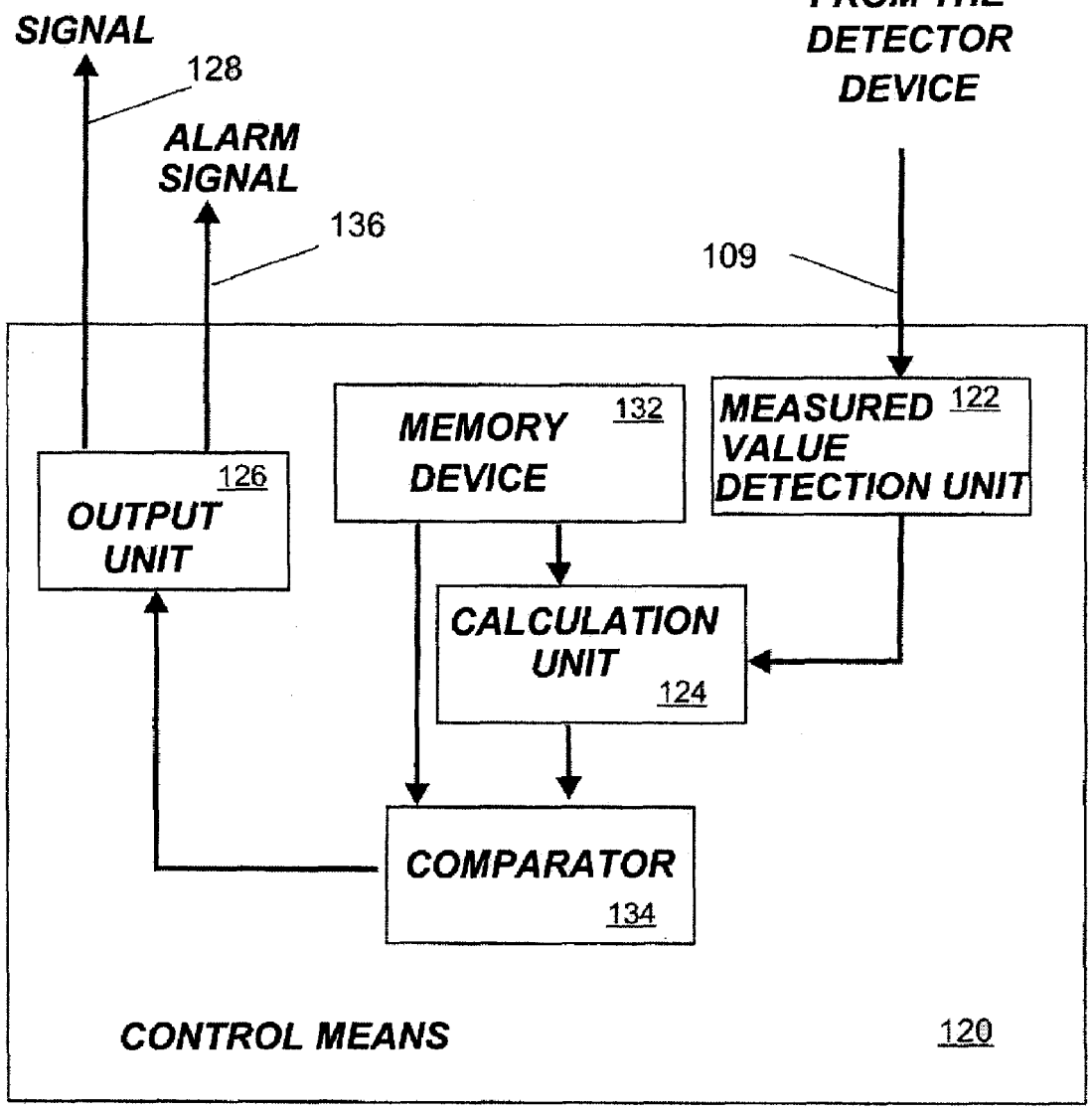
FIG. 4 is a schematic view of a control means according to the present invention.

FIG. 4 shows schematically the basic functional units provided, according to the invention, in the control means 120 from FIG. 1. The control means comprises a measured value detection unit 122 which detects the detector signal 109 supplied by the detector device. The detected signals are supplied to a calculation unit 124 in which an estimated value for the average, i.e. the integrated, measured value is calculated during the first pulse with the aid of information, stored in a memory device 132, concerning the curve of the detector signal 109 during a pulse. A comparator 134 compares the estimated value to a threshold value stored in the memory device and causes the output unit 126 to issue an alarm signal 136 if the stored threshold value was exceeded. The control means 120 may also be operated to predict, on the basis of the estimated integral value 302, an end value for the integral value in the settled state and to compare the correspondingly estimated end value to a stored threshold value for the end value.

Should an early warning not be required, the detector device supplies further detector signals 109 and the calculation unit 124 supplies, on the basis of these new estimated values during the integration phase, a constantly improved estimated value for the average measured value during the first pulse until, eventually, the estimated value supplied by the calculation unit corresponds to the actual average measured value. This procedure is carried out for all of the further pulses during the thermal settling process, so after a defined number of pulses a measurement signal is provided which may be issued as the end value.

According to the invention, an early warning may therefore be carried out in a gas sensor assembly, in the event of safety-relevant applications, if there is a hazardous concentration of gas as soon as the gas sensor system is started up. This may be achieved in an advantageous manner without increasing the complexity of the sensor assembly.

Measures to further improve precision, such as, for example, the use of more than one infrared radiation source or a plurality of detectors, may, of course, also be used in conjunction with the method according to the invention.

What is claimed is:

1. A system for measuring the presence and/or the concentration of an analyte using a gas sensor assembly comprising:
   at least one radiation source emitting radiation;
   a gas measurement chamber which may be filled with a test gas containing at least one analyte to be measured;
   at least one detector which detects the radiation and generates an output signal which is dependent on the presence and/or the concentration of the analyte,
   wherein the radiation source emits radiation in the form of pulses and, during each radiation pulse, a plurality of individual values are recorded for generating an average measured value,
   the first of the plurality of individual values being compared, during the first radiation pulse, with a predetermined threshold value and an alarm signal being generated if the threshold value is exceeded.

2. The system according to claim 1, wherein the comparison with the threshold value includes forming an estimated value for the average measured value of the first pulse and comparing the estimated value with a threshold value formed by a maximum permissible average measured value.

3. The system according to claim 2, wherein the comparison with the threshold value comprises forming a further estimated value for an end value achieved after thermal settling of the gas sensor assembly and comparing the further estimated value with a threshold value formed by a maximum permissible end value.

4. The system according to claim 3, wherein the estimated value for the end value achieved after the thermal settling is calculated on the basis of a stored thermal model of the detector device.

5. The system according to claim 3, wherein the temperature at the wall of the gas measurement chamber or in proximity to the radiation source is additionally measured and the measured temperature is used for correcting the measured values and/or for determining the achievement of the thermal equilibrium.

6. The system according to claim 2, wherein the average measured value is calculated by integration of a plurality of individual values during the radiation pulse.

7. The system according to claim 6, wherein a modified further estimated value for the end value achieved after the thermal settling is calculated on the basis of the actually measured average measured value of each successive radiation pulse.

8. The system according to claim 6, wherein the comparing of the first of the plurality of individual values with a predetermined threshold value and of generating an alarm signal if the threshold value is exceeded is repeated for at least one successive radiation pulse.

9. The system according to claim 6, wherein, after a predetermined number of radiation pulses, an output signal is issued if an alarm signal is not issued during the predetermined number of radiation pulses.

10. The system according to claim 2, wherein a modified estimated value for the average measured value is calculated on the basis of each successive individual value within a radiation pulse.

11. The system according to claim 1, wherein the at least one radiation source emits infrared radiation.

12. The system according to claim 1, wherein gaseous analytes are detected and/or the concentration thereof is determined.

13. The system according to claim 12, wherein the analyte is a polar gas, preferably carbon dioxide.

14. The system according to claim 1, wherein the detector comprises a pyro-element, a thermopile detector and/or a photodiode.

* * * * *